United States Patent
Jo et al.

(10) Patent No.: US 11,370,746 B2
(45) Date of Patent: Jun. 28, 2022

(54) GRANULES COMPRISING L-AMINO ACID AND METHOD FOR PREPARING THE SAME

(71) Applicant: CJ CHEILJEDANG CORPORATION, Seoul (KR)

(72) Inventors: Se-Hee Jo, Seoul (KR); Il Chul Kim, Seoul (KR); In Sung Lee, Seoul (KR); Yong Bum Seo, Seoul (KR); Kang Hoon Lee, Seoul (KR); Jaeik Kim, Seoul (KR); Jae Hun Yu, Seoul (KR); Min Kyung Kwon, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/981,871

(22) PCT Filed: Mar. 22, 2019

(86) PCT No.: PCT/KR2019/003387
§ 371 (c)(1),
(2) Date: Sep. 17, 2020

(87) PCT Pub. No.: WO2019/182413
PCT Pub. Date: Sep. 26, 2019

(65) Prior Publication Data
US 2021/0094903 A1    Apr. 1, 2021

(30) Foreign Application Priority Data
Mar. 23, 2018  (KR) .................. 10-2018-0033925

(51) Int. Cl.
*C07C 227/40*  (2006.01)
(52) U.S. Cl.
CPC .................. *C07C 227/40* (2013.01)
(58) Field of Classification Search
CPC ..... A23K 20/142; A23K 40/10; A23L 33/175; A23P 10/20; C07C 227/40; A61K 31/198; A61K 9/1688; A61K 9/1682; C12P 13/08
See application file for complete search history.

(56) References Cited

U.S. PATENT DOCUMENTS

| | | | |
|---|---|---|---|
| 4,777,051 A | 10/1988 | Nagano et al. | |
| 5,840,358 A | 11/1998 | Hofler et al. | |
| 5,935,635 A * | 8/1999 | Mori | A23K 20/28 426/656 |
| 5,990,350 A * | 11/1999 | Stevens | A23K 20/142 562/562 |
| 7,504,242 B2 | 3/2009 | Dunican et al. | |
| 7,863,435 B2 | 1/2011 | Park et al. | |
| 2005/0220933 A1* | 10/2005 | Hong | A23K 40/10 426/2 |
| 2015/0283527 A1 | 10/2015 | Alt et al. | |

FOREIGN PATENT DOCUMENTS

| | | |
|---|---|---|
| EP | 0 491 638 A2 | 6/1992 |
| JP | 2001-309751 A | 11/2001 |
| KR | 10-0389974 B1 | 6/2003 |
| KR | 10-2005-0056668 A | 6/2005 |
| KR | 10-2005-0097678 A | 10/2005 |
| KR | 10-0838200 B1 | 6/2008 |
| KR | 10-2009-0106543 A | 10/2009 |
| KR | 10-1429814 B1 | 8/2014 |
| KR | 10-1429815 B1 | 8/2014 |
| KR | 10-1485222 B1 | 1/2015 |
| KR | 10-2016-0030053 A | 3/2016 |
| KR | 10-2016-0057462 A | 5/2016 |
| KR | 10-2016-0075671 A | 6/2016 |
| KR | 10-1689451 B1 | 1/2017 |
| WO | 2013/105800 A2 | 7/2013 |
| WO | 2015/199406 A1 | 12/2015 |
| WO | 2016/036209 A1 | 3/2016 |
| WO | 2016/182321 A1 | 11/2016 |

* cited by examiner

*Primary Examiner* — Yevgeny Valenrod
*Assistant Examiner* — Blaine G Doletski
(74) *Attorney, Agent, or Firm* — Seed IP Law Group LLP

(57) ABSTRACT

The present disclosure relates to granules comprising an L-amino acid and a method for preparing the same. The method may comprise:

(a) preparing a fermentation liquid of L-amino acid;

(b) removing moisture from the fermentation liquid of L-amino acid such that the solid content of the fermentation liquid of L-amino acid is in a range of 20% to 90%;

(c) forming granulated particles with a moisture content of 0% to 40% by mixing the concentrated fermentation liquid of L-amino acid with a seed;

(d) drying the granulated particles formed in Step (c);

(e) sieving the granulated particles dried in Step (d); and (f) pulverizing or circulating the particles left in step (e) to be recycled as the seed in step (c).

13 Claims, No Drawings

GRANULES COMPRISING L-AMINO ACID AND METHOD FOR PREPARING THE SAME

TECHNICAL FIELD

The present disclosure relates to granules comprising an L-amino acid, and a method for preparing the same.

BACKGROUND ART

L-Amino acids are basic structural units of proteins and are used as important materials for pharmaceutical raw materials and food additives, animal feed, nutrients, pesticides, bactericides, etc. Among them, L-threonine, which is an essential amino acid not biosynthesized in vivo at all, is widely used in feeds and food additives and is also used as a synthetic raw material for infusions and pharmaceuticals for medical use. L-Threonine is mainly produced by a fermentation method using a microorganism of the genus *Escherichia*, the genus *Serratia*, the genus *Providencia*, or the genus *Corynebacterium*, or an artificial strain thereof developed by artificial mutation or genetic recombination methods.

However, the fermentation described above produces not only L-threonine, but also by-products and waste. Therefore, in order to obtain highly purified L-threonine, it is essential to perform separation and purification steps after the step of a fermentation process. Meanwhile, since other products contained in a fermentation liquid also contain nutritionally valuable ingredients, there is a growing demand for products containing the entire fermentation liquid, particularly products in the form of granular products convenient for storage, portability, ingestion, etc.

For the granulation of a fermentation liquid, all of the moisture in the fermentation liquid must be evaporated before the preparation of granules, and it is necessary to evaporate as much moisture as possible during the concentration process so as to reduce the amount of steam used for granulation. The use of a fluidized bed granulator for preparing granule products for feed additives has been disclosed in many documents (EPA 0491638, KR 10-1052573, KR 10-0838200, and US 2015-0283527). In the case of lysine, due to its high solubility, crystals are not produced even when the moisture is evaporated until the solid content of the fermentation liquid becomes about 40% to about 55% (a moisture content of 45% to 60%). Therefore, granulation can be achieved by the fluidized bed granulation method where the liquid is sprayed through a nozzle. However, in the case of the fermentation liquid of threonine with a low solubility, crystals are produced even when the solid content as low as in a range of about 18% to about 22% (a moisture content of 78% to 82%). Therefore, a large amount of moisture must be evaporated during the drying process, thus resulting in consumption of a large amount of steam.

DISCLOSURE

Technical Problem

The present inventors have made extensive efforts to prepare granules of an L-amino acid in an excellent efficiency from a fermentation liquid of the L-amino acid. As a result, they have developed a method for preparing L-amino acid granules with an excellent production efficiency even when a fermentation liquid with a high solid content is used, thereby completing the present disclosure.

Technical Solution

An object of the present disclosure is to provide a method for preparing L-amino acid granules, which comprises a step of concentrating a fermentation liquid of an L-amino acid.

Advantageous Effects

The method of the present disclosure for preparing L-amino acid granules shows an excellent production efficiency even when a fermentation liquid with a high solid content is used, and thus, it can contribute significantly to cost reduction in the production of amino acid granules.

Best Mode for Carrying Out the Invention

The present disclosure is described in detail as follows. Meanwhile, respective descriptions and embodiments disclosed in the present disclosure may also be applied to other descriptions and embodiments. That is, all combinations of various elements disclosed in the present disclosure fall within the scope of the present disclosure. Further, the scope of the present disclosure is not limited by the specific description below.

To achieve the above object, the present disclosure provides a method for preparing L-amino acid granules, which comprises a step of concentrating a fermentation liquid of an L-amino acid.

An object of the present disclosure is to economically prepare L-amino acid granules using a fermentation liquid of a microorganism that produces an L-amino acid with a higher productivity.

In order to increase the productivity of granules prepared from a fermentation liquid, it is important to reduce the amount of steam used in the processes of concentration and drying of a fermentation liquid. That is, it is important to reduce the amount of steam to be used by minimizing the amount of moisture to be evaporated in the processes of granulation and drying by evaporating as much moisture as possible in a step preceding the granulation process.

However, for a fermentation liquid of an amino acid with a low solubility (e.g., L-threonine) to pass through a spray nozzle, the solid content in the liquid must be low while the moisture content in the liquid must be high. Therefore, the amount of moisture to be evaporated in the processes of granulation and drying to be performed will increase significantly. Finally, a large amount of steam is consumed to produce granules. That is, for amino acids with a low solubility, since it is not possible to evaporate a large amount of moisture during concentration and drying, there are problems in that the manufacturing time and process are complicated and the production efficiency is decreased, leading to an increase in the manufacturing cost.

In the present disclosure, since a large amount of moisture can be evaporated during concentration, granulation can easily be performed even when a fermentation liquid has a high solid content. Therefore, the present disclosure provides a method for reducing steam consumption while increasing the efficiency of granule production. Additionally, the present disclosure proposes a method, in which the amount of a fermentation liquid to be injected into a granulator is increased by reducing the circulation rate of a seed by performing the granulation through a mixed granulation method where a concentrated fermentation liquid is mixed with the seed, whereas the moisture content of the granules to be discharged from the granulator is decreased, thus making it possible to increase the productivity of granulation.

Specifically, the method for preparing L-amino acid granules according to the present disclosure may include the following steps:
- (a) a step of preparing a fermentation liquid of an L-amino acid (a fermentation liquid preparation step);
- (b) a step of removing moisture from the fermentation liquid of the L-amino acid such that the solid content of the fermentation liquid of the L-amino acid is in a range of 40% to 80% (a concentration step);
- (c) a step of forming granulated particles with a moisture content of 5% to 20% by mixing the concentrated fermentation liquid of the L-amino acid with a seed (a granule forming step);
- (d) a step of drying the granulated particles formed in step (c) (a drying step);
- (e) a step of sieving the granulated particles dried in step (d) (a sieving step); and
- (f) a step of pulverizing and/or circulating the particles left in step (e) to be reused as the seed in step (c) (a seed circulating step).

As used herein, the term "L-amino acid" includes, without limitation, any amino acid that can be used in the method for preparing granules according to the present disclosure. For example, the L-amino acid may be one or more selected from the group consisting of L-threonine, L-tryptophan, L-methionine, L-valine, L-tyrosine, L-phenylalanine, L-isoleucine, and L-leucine, but the L-amino acid is not limited thereto.

In the present disclosure, step (a) above is a step of preparing a fermentation liquid of an L-amino acid. In particular, the fermentation liquid of an L-amino acid may refer to a medium obtained by culturing a microorganism producing an L-amino acid, a cultured product including the culture medium or a microorganism cultured therewith, etc.

Specifically, the fermentation liquid may be obtained by culturing or fermenting a microorganism producing an L-amino acid, and the microorganism and the method for culturing/fermenting the microorganism are known in the art and may be selected and used by those skilled in the art. The microorganism includes both wild-type microorganisms and microorganisms in which a natural or artificial genetic modification has occurred. The microorganism may be one in which a specific mechanism is weakened or enhanced due to causes (e.g., insertion of a foreign gene, enhancement of the activity of an endogenous gene, inactivation of the activity of an endogenous gene, etc.), and may be a microorganism in which, for the production of a desired L-amino acid, a genetic mutation has occurred or an activity associated therewith has been enhanced (KR 2005-0056668 A, KR 10-1689451 B, KR 2015-0125440 A, US 7504242 B, KR 1485222 B, KR 1429815 B, KR 1429814 B, WO 2015-199406 A, WO 2016-182321 A, WO 2016-036209 A, WO 2013-105800 A, etc.). Specific examples of the microorganism producing an L-amino acid may include those which belong to the genus *Brevibacterium*, the genus *Corynebacterium*, the genus *Escherichia*, the genus *Serratia*, the genus *Erwinia*, the genus *Enterobacteria*, the genus *Streptomyces*, the genus *Pseudomonas*, etc. More specifically, the microorganism may be a microorganism of the genus *Corynebacterium*, which is a generally recognized as safe (GRAS) strain, and the desired L-amino acid may be obtained by fermentation, but the microorganism is not limited thereto. Even more specifically, the microorganism may be *Corynebacterium glutamicum*, but the microorganism is not limited thereto.

Step (b) above is a step of removing by evaporation the moisture in the fermentation liquid of the L-amino acid obtained in step (a) above, and it is a step of concentrating or drying the fermentation liquid.

This step is the most important process to minimize the amount of steam consumed in the production of granules. In the conventional granule preparation method, the method had to be performed by adjusting the content of solids contained in the slurry to be in a range of about 40% to about 55% for amino acids with a high solubility, and by adjusting the content of solids contained in the slurry to be in a range of about 18% to about 22% for amino acids with a low solubility. However, the granule preparation method according to the present disclosure is characterized in that the productivity and production efficiency of the overall preparation process are increased even when the amino acid is an amino acid with a low solubility, by reducing the amount of steam to be used through evaporation of a large amount of moisture during concentration by adjusting the content of the solids contained in the slurry to be in a range of 40% to 80%.

Specifically, the moisture in the fermentation liquid may be removed such that the content of solids contained in the slurry is in a range of 20% (v/v) to 90% (v/v), preferably 30% (v/v) to 85% (v/v), and more preferably 40% (v/v) to 80% (v/v), but the preferred solid content is not limited thereto. When the content of solids is adjusted to below the above range, there are problems of overloading of the process and excessive use of steam in the subsequent process during granulation, whereas when the content of solids is adjusted to beyond the above range, it may be difficult to transport the slurry due to its high viscosity.

Specifically, step (b) above may be a step in which the moisture in the fermentation liquid is removed such that the fermentation liquid of the L-amino acid is adjusted to have a solid content in a range of 40% to 80%, and accordingly, a concentrated fermentation liquid (e.g., a slurry) can be produced.

In this step, as the method for removing moisture, a method known in the art may be used, and specifically, the method may be performed in a concentration method or slurry-drying method, and the concentration may be performed along with a step of reducing pressure, but the method is not limited thereto.

For example, the method for removing moisture may be performed using any facility that can evaporate a fermentation liquid, and the facility may be appropriately selected and used by those skilled in the art. Specifically, a forced circulation concentration pipe may be used, and a paddle dryer, a slurry-drying facility, etc. may be used, but the facility is not limited thereto.

Meanwhile, the method of the present disclosure for preparing L-threonine granules, after the concentration step of step (b) above, may further include: (i) a step of separating solids from a slurry concentrated in step (b) above (a solid separation step); and (ii) a step of removing moisture from the slurry remaining after separating the solids such that the slurry has a solid content lower than that in step (b) above, and mixing the resulting slurry with the solids in step (i) above (a re-concentration step). Specifically, the method may further include (i) a step of separating solids from a slurry concentrated in step (b) above (a solid separation step); and (ii) a step of removing moisture from the slurry remaining after separating the solids such that the slurry has a solid content in a range of 30% to 60%, and mixing the resulting slurry with the solids in step (i) above (a re-concentration step). The above step is a process of increasing the productivity of L-amino acid granules by performing an additional concentration step after concentrating the fermentation liquid. Specifically, the above step may be a step of increasing the content of solids by separating the solids precipitated during or after the concentration of the fermentation liquid of step (b) above, and then mixing the remaining slurry with the re-concentrated slurry or granulated particles formed. In addition, the above steps may be continuously performed, but are not limited thereto. While it was not possible to perform granulation by increasing the solid content in a conventional granulation method, productivity can be increased by performing concentration and granulation to have a high solid content in the preparation method of the present disclosure.

Step (i) above is a step of separating the solids produced through step (b) above, and the solids can be used in subsequent step (ii) or steps (c) to (f).

Step (ii) above is a step of removing moisture from the slurry remaining after separating the solids produced through step (b) above followed by mixing the resulting slurry with the separated solids.

Specifically, the moisture contained in the slurry may be removed such that the content of the solids contained in the remaining slurry is in a range of 40% (v/v) to 80% (v/v), specifically 35% (v/v) 70% (v/v), and more specifically 30% (v/v) to 60% (v/v), but the preferred solid content is not limited thereto. When the solid content is adjusted to below the above range, there are problems of overloading of the process and excessive use of steam in the subsequent process during granulation, whereas when the content of solids is adjusted to beyond the above range, it may be difficult to transport the slurry due to its high viscosity.

Additionally, as the method for removing moisture in step (ii) above, a method known in the art may be used, and specifically, the method may be performed in a concentration method or slurry-drying method, and the concentration may be performed along with a step of reducing pressure, but the method is not limited thereto.

Step (c) above is a step of forming granulated particles using the slurry of the fermentation liquid of an L-amino acid obtained in step (b) above, and specifically, it is a process of mixing the slurry with a seed.

As used herein, the term "seed", which is also called a crystal of a seed or a seed crystal, refers to a material used as a catalyst for crystallization or granulation of a liquid. Specifically, the seed in the present disclosure may refer to a crystal of an L-amino acid, but the seed is not limited thereto. When the seed and a slurry of a fermentation liquid meet, the solid components present in the fermentation liquid are combined with the seed to form an aggregation, thereby forming granules.

The moisture content of granulated particles formed in this step may be in a range of 0% (v/v) to 40% (v/v), specifically 1% (v/v) to 30% (v/v), more specifically 3% (v/v) to 25% (v/v), even more specifically 5% (v/v) to 20% (v/v), and most specifically 5% (v/v) to 15% (v/v), but the moisture content is not limited thereto. In particular, the moisture content is the most important factor in increasing the productivity with respect to the granule preparation method according to the present disclosure. When the moisture content of the granulated particles is below the above range, the amount of a slurry that can be processed in a granulator decreases compared to the weight of the unit seed, thus becoming a cause of decreased productivity. In contrast, when the moisture content of the granulated particles is beyond the above range, the granulated particles discharged from the granulator are in a state of a paste instead of granules, and thus, it is impossible to perform drying in a fluidized bed dryer.

In the present disclosure, the moisture content of the granulated particles may be determined by the particle size of a seed. Specifically, as the particle size of the seed becomes smaller, the moisture content of the granulated particles may increase, and as the particle size of the seed becomes larger, the moisture content of the granulated particles may decrease. More specifically, the seed may be one in which the particles with a particle size of 10 μm or less, specifically 90 μm or less, and more specifically 75 μm or less are present in a range of 9% or higher relative to the entire seed. Alternatively, the seed may be one in which the particles with a particle size of 75 μm or less are present in a range of 5% or higher, specifically 7% or higher, and more specifically 9% or higher relative to the entire seed, but the seed is not limited thereto. Alternatively, the seed may be one in which the particles with a particle size of 212 μm or less are present in a range of 100% or less, and specifically 97% or less relative to the entire seed, but the seed is not limited thereto. Alternatively, the seed may be one in which the particles with a particle size of 75 μm or less are present in a range of 5% or higher and the particles with a particle size of 212 μm or less are present in a range of 100% or less relative to the entire seed; or more specifically, the seed may be one in which the particles with a particle size of 75 μm or less are present in a range of 9% or higher and the particles with a particle size of 212 μm or less are present in a range of 97% or less relative to the entire seed, but the seed is not limited thereto.

Additionally, the moisture content may be determined by the amount of the slurry of the concentrated fermentation liquid injected. Specifically, as the amount of the slurry injected increases, the moisture content of the granulated particles may increase, and as the amount of the slurry injected decreases, the moisture content of the granulated particles may decrease. Since the amount of the slurry to be injected is determined according to the scale of the slurry of the fermentation liquid, those skilled in the art can appropriately select and determine the amount to be injected.

The size of the granulated particles formed in this step can be adjusted by the particle size of the seed or the mixing ratio of the seed to the slurry. The particle size of the seed is as described above. The "mixing ratio of a seed to a slurry" may be one which is calculated as the total amount of the seed to be injected and mixed relative to the total amount of the slurry to be injected. For example, the mixing ratio of a seed to a slurry may be in a range of 1 to 15, specifically 1.5 to 10, and more specifically 2.2 to 9, but the mixing ratio is not limited thereto.

The "mixing ratio of a seed to a slurry" may also be calculated by a "mixing ratio of a seed to the solid content of a slurry". Specifically, it may be calculated as the total amount of the seed to be injected and mixed relative to the total amount of the solids in the slurry to be injected. For example, the mixing ratio of a seed to the solid content of a slurry may be in a range of 1 to 30, specifically 2 to 25, and more specifically 2.8 to 22, but the mixing ratio is not limited thereto.

The expression of the "mixing ratio of a seed to a slurry" or the "mixing ratio of a seed to the solid content of a slurry" may be used interchangeably with the expression of "ratio of a seed to be injected".

Additionally, with respect to the particle size of the granulated particles obtained in step (c) above, the particles with a particle size of 2,000 μm or higher may be present in an amount of 5.0% or less, specifically 3.0% or less, and more specifically 1.0% or less; and the particles with a particle size of 75 μm or less may be present in a range of 20.0% or less, specifically 15.0% or less, and more specifically 5.0%, but these are not limited thereto.

Additionally, with respect to the particle size of the granulated particles of step (c) above, the particles with a particle size greater than 75 μm may be present in a range of 50% or higher, but the particle size of the granulated particles is not limited thereto.

Step (d) above is a step of drying the granulated particles formed in step (c) above, and specifically, it is a step of finally removing the moisture caused by the fermentation liquid.

In this step, the method of drying is not particularly limited, but any method known in the art may be used. For example, the drying temperature (material temperature) may be in a range of 50° C. to 100° C., specifically 55° C. to 95° C., and more specifically 60° C. to 90° C., but the drying temperature is not limited thereto.

Step (e) above is a process of sieving the granulated particles dried in step (d) above, and the granulated particles can be sieved based on the desired particle size.

Specifically, the desired particle size of the granulated particles to be sieved may be appropriately selected according to the selection by those skilled in the art. Specifically, the desired particle size may be in a range of 50 μm to 3,000 μm, more specifically 75 μm to 2,000 μm, and even more specifically 100 μm to 2,000 μm, but the desired particle size is not limited thereto. Granules with a particle size other than those described above cannot exhibit proper properties as a granulated product containing an amino acid, and thus, it is difficult to develop them into a product.

Step (f) above is a step of recycling the particles, which remain after sieving in step (e) above, in step (c) above, and it is a process of pulverizing and/or circulating granulated particles without a desired particle size. Specifically, the granulated particles remaining after sieving or the pulverized particles thereof may be recycled as a seed in step (c) above.

For example, the granulated particles used in this step may be granulated particles which have a particle size other than those in which the particles with a particle size of 2,000 μm or higher are present in an amount of 1.0% or less and the particles with a particle size of 75 μm or less are present in an amount of 1.5% or less, but the granulated particles used in this step are not limited thereto. Specifically, the granulated particles remaining after sieving may be granulated particles which have a particle size other than those in which the particles with a particle size of 2,000 μm or higher are present in an amount of 1.0% or less and the particles with a particle size of 75 μm or less are present in an amount of 1.5% or less, but the granulated particles remaining after sieving are not limited thereto.

Additionally, the method for pulverizing and/or circulating the granulated particles is not particularly limited, but any method known in the art may be used.

The L-amino acid granules of the present disclosure are granulated particles containing an L-amino acid as an active ingredient, and they may further contain ingredients other than the L-amino acid in a fermentation liquid of an L-amino acid. For example, the granulated particles may further contain a microorganism used in the culture, but the granulated particles are not limited thereto.

DETAILED DESCRIPTION OF THE INVENTION

Hereinafter, the present disclosure will be described in detail through exemplary embodiments. However, these exemplary embodiments are for illustrative purposes only and are not intended to limit the scope of the present disclosure.

EXAMPLE 1

Concentration and Granulation of Fermentation Liquid

EXAMPLE 1-1

Concentration of Fermentation Liquid

In order to prepare granules containing L-threonine in this granulation process, a fermentation liquid having the following composition was obtained by culturing a microorganism producing L-threonine.

The fermentation liquid contained a cultured medium and a microorganism, and moisture measurement and composition analysis were performed using the same. The composition analysis shown in Table 1 below was performed after removing the cells of the microorganism for LC analysis.

TABLE 1

| Composition | Value |
| --- | --- |
| Threonine | 174.7 g/L |
| Amino Acids Other Than Threonine | 5.8 g/L |
| Carboxylic Acid (8 carbon atoms or less) | 0.3 g/L |
| Inorganic Materials | 6.3 g/L |
| Moisture Content | 77.8% |

The moisture in the fermentation liquid of a microorganism was removed by concentrating the fermentation liquid under reduced pressure. Specifically, as shown in Table 2, the concentration of the solids was performed variously to be in a range of 40.3% to 79.4%, and thereby slurries of the fermentation liquid were prepared.

Additionally, based on the determination that a solid content of 40% or less is not efficient in terms of productivity and the amount of steam consumption, and that a solid content of 80% or higher will cause a difficulty in slurry transportation, etc., the solid content was adjusted to be in a range of 40.3% to 79.4%.

Meanwhile, the seeds were prepared such that the fermentation liquid was pre-dried in advance and then pulverized so that the particles with a particle size of 75 μm or less were present in a range of 9% or more.

EXAMPLE 1-2

Confirmation of Changes in Particle Size of Granules According to Solid Content of Fermentation Liquid The slurries of the fermentation liquid and the seeds, which were prepared in Example 1-1, were injected into a granulator to perform granulation. The mixed-type granulator used in this granulation process was a CM5 model (Lodige), and the obtained wet granules were dried with a fluidized bed dryer (GR Engineering).

Meanwhile, before performing the granulation, the seed injection rate and the slurry injection rate were measured in advance so as to set the moisture level of the wet granules being discharged from the granulator at a level around 7%. The subsequent experimental conditions and results are shown in Table 2 below.

It was confirmed that the overall particle size distribution of granules and the L-threonine content had no significant effect on the solid content of the fermentation liquid. That is, it was confirmed that a fermentation liquid with a low solubility could also increase productivity by performing the granulation in a state with a high solid content. Since the particles of 2,000 μm or more were present in a range of 1.0% or less and the particles of 75 μm or less were all present in a range of 5.0% or less, it was confirmed that granulated particles with appropriate quality for commercialization can be obtained using the granulation method of the present disclosure.

TABLE 2

| Granulation Conditions | | | | | | | |
|---|---|---|---|---|---|---|---|
| Solid Content of Slurry | % | — | 40.3 | 51.2 | 60.3 | 66.7 | 79.4 |
| Amount of Slurry Injection | kg/hr | — | 7.7 | 9.9 | 12.1 | 15.9 | 29.8 |
| Seed Injection Rate | kg/hr | — | 65.8 | 65.8 | 65.8 | 65.8 | 65.8 |
| Moisture Content of Seed | % | — | 0.8 | 0.8 | 0.8 | 0.8 | 0.8 |
| Seed Injection Ratio (Seed to Solid Content of Slurry) | — | — | 21.2 | 13.0 | 9.0 | 6.2 | 2.8 |
| Seed Injection Ratio (Seed to Slurry) | — | — | 8.5 | 6.6 | 5.2 | 4.1 | 2.2 |
| Moisture Content of Wet Granules | % | — | 7.0 | 7.2 | 7.0 | 7.1 | 7.1 |

| Type | | Seed | Analysis Results of Granulated Particles According to Conditions | | | | |
|---|---|---|---|---|---|---|---|
| L-threonine Content | % | 78.2 | 77.9 | 77.8 | 77.5 | 78.1 | 78.2 |
| Apparent Density | kg/m³ | 652 | 775 | 753 | 762 | 795 | 765 |
| Moisture Content | % | 0.8 | 1.5 | 1.3 | 1.0 | 0.8 | 0.9 |
| Protein Content | % | 12.5 | 12.3 | 12.4 | 12.2 | 12.6 | 12.7 |

| Range of Particle Size (μm) | | Particle Size Distribution | | | | | |
|---|---|---|---|---|---|---|---|
| ≥2,000 | % | 0.0 | 0.3 | 0.2 | 0.5 | 0.3 | 0.1 |
| 1,000 ≤ X ≤ 2,000 | | 0.0 | 1.7 | 1.8 | 1.6 | 1.6 | 1.4 |

TABLE 2-continued

| 750 ≤ X ≤ 1,000 | 0.8 | 5.9 | 6.2 | 5.7 | 6.3 | 5.5 |
|---|---|---|---|---|---|---|
| 500 ≤ X ≤ 750 | 18.6 | 33.6 | 30.0 | 34.2 | 32.1 | 31.2 |
| 350 ≤ X ≤ 500 | 26.3 | 45.1 | 43.2 | 40.0 | 43.3 | 45.2 |
| 212 ≤ X ≤ 350 | 33.0 | 10.3 | 15.1 | 14.5 | 12.3 | 13.3 |
| 75 ≤ X ≤ 212 | 12.1 | 2.6 | 2.0 | 2.5 | 2.7 | 2.1 |
| 0 ≤ X ≤ 75 | 9.1 | 0.5 | 1.5 | 1.0 | 1.4 | 1.2 |
| Total | 100.0 | 100.0 | 100.0 | 100.0 | 100.0 | 100.0 |

EXAMPLE 2

Confirmation of Changes in Particle Size of Granules According to Amount of Slurry Injection In order to confirm that the particle size of granules can be adjusted according to the mixing ratio of a seed and a slurry of a fermentation liquid, an experiment was performed as follows. A fermentation liquid of threonine was concentrated under reduced pressure. Then, granulation was performed by varying the injected amount of the threonine slurry, which was concentrated to have a solid content of 63.2%, while fixing the particle size and injection rate of the seed, and the resulting moisture content and particle size of the granules before drying are shown in Table 3 below. In order to more clearly confirm the changes in the particle size of granules according to an increase in the injected amount of the slurry (the amount of the slurry or the solid content of the slurry), a seed with an extremely large amount of fine particles was used. A seed in which particles with a particle size of 212 μm or less were present in 97.9% was used. As shown in Table 3, it was confirmed that the particle size was increased as a whole while the seed injection ratio was decreased according to the injected amount. In addition, the moisture content of the granules before drying varied within a range of 5% to 12.8% according to the changes in the injected amount. In contrast, it was confirmed that under the condition of a moisture content of 15%, the particles were in a state of a paste rather than granules, and thus the drying in a fluid bed dryer was impossible.

Taken together, it was confirmed that under certain specific seed conditions, the seed injection ratio decreased as the amount of the slurry of the fermentation liquid injected increased, and the moisture content of wet granules before drying increased, and additionally, the particle size of the granulated products showed a tendency of growth.

From the above results, it was confirmed that the particle size of granulated particles and the moisture content of granules can be controlled according to the amount of the slurry of the fermentation liquid injected. In addition, it may be interpreted that it is possible to control the moisture content of granules and the particle size of granulated particles according to the ratio of seed injection to a slurry.

TABLE 3

| Granulation Conditions | | | | | | | |
|---|---|---|---|---|---|---|---|
| Solid Content of Slurry | % | — | 63.2 | 63.2 | 63.2 | 63.2 | 63.2 |
| Amount of Slurry Injection | kg/hr | — | 7.7 | 12.4 | 17.5 | 23.6 | 30.8 |
| Seed Injection Rate | kg/hr | — | 62.2 | 62.2 | 62.2 | 62.2 | 62.2 |
| Moisture Content of Seed | % | — | 1.1 | 1.1 | 1.1 | 1.1 | 1.1 |
| Seed Injection Ratio (Seed to Solid Content of Slurry) | — | — | 12.8 | 7.9 | 5.6 | 4.2 | 3.2 |
| Seed Injection Ratio (Seed to Slurry) | — | — | 8.1 | 5.0 | 3.6 | 2.6 | 2.0 |

TABLE 3-continued

| Analysis of Granulated Particles After Granulation (Before Drying) | | | | | | | |
|---|---|---|---|---|---|---|---|
| Moisture Content of Wet Granules | % | — | 5.0 | 6.9 | 8.9 | 11.1 | 12.8 |
| Type | | Seed | Analysis of Granulated Particles After Drying | | | | |
| Range of Particle Size (μm) | | | Particle Size Distribution | | | | |
| ≥2,000 | % | 0.0 | 0.0 | 0.0 | 0.7 | 3.7 | 10.3 |
| 1,000 ≤ X ≤ 2,000 | | 0.0 | 0.0 | 0.0 | 5.5 | 8.8 | 26.5 |
| 750 ≤ X ≤ 1,000 | | 0.0 | 0.0 | 1.1 | 11.3 | 17.8 | 25.8 |
| 500 ≤ X ≤ 750 | | 0.0 | 0.0 | 5.9 | 26.3 | 31.8 | 17.2 |
| 350 ≤ X ≤ 500 | | 0.0 | 0.1 | 18.8 | 26.0 | 19.3 | 11.3 |
| 212 ≤ X ≤ 350 | | 2.1 | 10.1 | 33.2 | 16.2 | 10.2 | 5.2 |
| 75 ≤ X ≤ 212 | | 30.2 | 44.3 | 25.5 | 9.2 | 5.5 | 2.2 |
| 0 ≤ X ≤ 75 | | 67.7 | 45.5 | 15.5 | 4.8 | 2.9 | 1.5 |
| Total | | 100.0 | 100.0 | 100.0 | 100.0 | 100.0 | 100.0 |

EXAMPLE 3

Confirmation of Productivity According to Changes in Particle Size of Seed

The productivity of the granule preparation method of the present disclosure increases as the amount of the slurry of the fermentation liquid increases relative to the amount of a unit seed. However, when the ratio of slurry injection increases, the particles being discharged from a granulator undergo conversion to a state of a paste as the amount of slurry injection reaches a certain level or higher, and when the amount of slurry injection increases further, the particles are converted further to a slurry state. When the granules are in a slurry state or a paste-like state, it is difficult to dry the granules in a fluidized bed dryer, and an agglomerated mass of granules is generated, which becomes the most serious cause of trouble for the dryer.

In this Example, with respect to the method of increasing productivity, the maximum amount of slurry injection compared to the seed amount according to the changes in particle size of the seed was confirmed.

In order to allow variations in the particle size of the seed, granulated particles were used by recirculating them as the seed, and the circulation was performed 3 times in total. The solid content of the slurry of a fermentation liquid used was 59.6%. With respect to the particle size distribution of the initial seed, a seed with an extremely large amount of particles was used as the primary seed as shown in Table 4, and the obtained granules were used as a seed in the next circulation, thereby allowing the particle size of the seed of a subsequent circulation to increase. As mentioned, when the amount of slurry injection increases, the moisture being discharged from a granulator increases, thus making it difficult to dry the particles in a fluidized bed dryer. Therefore, this Example was performed by confirming the maximum injected amount of the slurry under which the particles discharged from a granulator can be dried in a fluidized bed dryer, and the values are shown in Table 4.

It was confirmed that as the circulation continued, the particle size of the granulated products and the seeds used in the granules of the subsequent circulations increased, and as a result, the amount of slurry injection per seed amount decreased, thus resulting in a decrease of the moisture content of wet granules.

That is, it was found that as the particle size of the seeds increased, the amount of slurry injection decreased, and when the particle size of the seeds became too large, the amount of slurry injection became too low and the seed injection ratio became relatively high, thereby resulting in decreased productivity.

From these results, it was confirmed that the particle size of granules can be adjusted by the particle size of a seed or the mixing ratio of a seed to a slurry.

TABLE 4

| | | Granulation Conditions | | | | |
|---|---|---|---|---|---|---|
| Solid Content of Slurry | % | — | 59.6 | 59.6 | 59.6 | 59.6 |
| Amount of Slurry Injection | kg/hr | — | 35.4 | 19.7 | 8.8 | 5.7 |
| Seed Injection Rate | kg/hr | — | 52.3 | 53.5 | 54.2 | 53.7 |
| Moisture Content of Seed | % | — | 1.8 | 1.5 | 1.3 | 1.0 |
| Seed Injection Ratio (Seed to Solid Content of Slurry) | | — | 2.5 | 4.6 | 10.3 | 15.8 |
| Seed Injection Ratio (Seed to Slurry) | | | 1.5 | 2.7 | 6.2 | 9.4 |

TABLE 4-continued

| After Granulation (Before Drying) | | | | | |
|---|---|---|---|---|---|
| Moisture Content of Wet Granules | % | — | 17.4 | 11.8 | 6.8 | 4.7 |

| | Particle Size Distribution | | | | |
|---|---|---|---|---|---|
| Range of Particle Size (μm) | Primary Seed | Primary Granules (Secondary Seed) | Secondary Granules (Tertiary Seed) | Tertiary Granules (Quaternary Seed) | Quaternary Granules |
| ≥2,000 % | 0.0 | 0.0 | 0.0 | 0.6 | 1.3 |
| 1,000 ≤ X ≤ 2,000 | 0.0 | 0.0 | 0.4 | 2.0 | 3.7 |
| 750 ≤ X ≤ 1000 | 0.0 | 0.2 | 3.4 | 11.9 | 17.7 |
| 500 ≤ X ≤ 750 | 0.0 | 0.1 | 10.1 | 27.1 | 32.2 |
| 350 ≤ X ≤ 500 | 0.0 | 4.2 | 32.7 | 40.1 | 35.2 |
| 212 ≤ X ≤ 350 | 0.0 | 19.9 | 39.8 | 17.0 | 7.9 |
| 75 ≤ X ≤ 212 | 5.3 | 38.2 | 13.2 | 1.2 | 0.7 |
| 0 ≤ X ≤ 75 | 94.7 | 37.4 | 0.5 | 0.3 | 1.2 |
| Total | 100.0 | 100.0 | 100.0 | 100.0 | 100.0 |

EXAMPLE 4

Confirmation of Productivity According to Re-Concentration of Concentrated Fermentation Liquid This Example is an example related to a method for increasing productivity by separating the solids produced after concentrating a fermentation liquid, followed by further concentrating its mother liquor (supernatant). That is, after concentrating a fermentation liquid, the solids were separated and sent to a granulator using the SDC (PTM006™, Tomoe Engineering Co., Ltd.), and the filtrate, from which the solids were separated, was further concentrated and sent to a granulator to reduce the total amount of moisture being transferred to the granulator, thereby increasing the productivity of the granulator.

The fermentation liquid was concentrated to have a solid content of 60.1%, and then solids and the mother liquor were separated using the SDC. In particular, according to the measurement, the recovered solids were measured to have a moisture content of 18.1%, and the separated mother liquor had a solid content of 28.1%. The mother liquor was further concentrated under reduced pressure to have a solid content of 35%, 45%, and 55%, respectively, so as to prepare slurries of the mother liquor. Based on the amount of 1 kg of the separated solids, a slurry of the mother liquor was injected into a granulator according to the amount produced. The amount of seed injection to be injected into the granulator was adjusted so that the moisture content of wet granules could be at a level of 10.5%.

As a result of the granulation test, it was possible to obtain granules at a uniform level in all aspects relating to content, particle size distribution, and apparent density, regardless of the solid content of the mother liquor slurry. Specifically, regardless of the concentration degree of the mother liquor slurry, all of the particles having a particle size of 75 μm or less were present in less than 1.0%, and all of the particles having a particle size of 1,000 μm to 2,000 μm were present in less than 1.0%, so that more uniform and high-quality granulated products could be produced.

From these results, it was confirmed that L-amino acid granules can be produced with a higher productivity when the granulation process is performed in such a manner that the solids produced after concentrating a fermentation liquid are separated, the mother liquor is re-concentrated, and then the resulting mother liquor and the separated solids are mixed for granulation.

TABLE 5

| Granulation Conditions | | | | | |
|---|---|---|---|---|---|
| Mother Liquor Slurry | Solid Content | % | — | 34.8 | 45.5 | 54.4 |
| | Amount Injected | kg | — | 0.37 | 0.29 | 0.23 |
| Separated Solid Content | Moisture Content | % | — | 18.1 | 18.1 | 18.1 |
| | Amount Injected | kg | — | 1.0 | 1.0 | 1.0 |
| Seed | Moisture Content | % | — | 0.9 | 0.9 | 0.9 |
| | Amount Injected | kg | — | 2.9 | 2.1 | 1.6 |
| Moisture Content Before Drying | | % | — | 10.4 | 10.6 | 10.4 |
| Type | | | Seed | Granules After Drying | | |
| Content | | % | 76.3 | 76.5 | 76.3 | 76.4 |
| Apparent Density | | kg/m³ | 632 | 769 | 761 | 765 |

| Range of Particle Size (um) | Particle Size Distribution | | | | |
|---|---|---|---|---|---|
| ≥2,000 % | 0.0 | 0.0 | 0.0 | 0.1 |
| 1,000 ≤ X ≤ 2,000 | 0.0 | 0.2 | 0.5 | 0.4 |
| 750 ≤ X ≤ 1000 | 0.2 | 2.2 | 3.3 | 3.1 |
| 500 ≤ X ≤ 750 | 0.1 | 9.7 | 11.3 | 10.3 |
| 350 ≤ X ≤ 500 | 4.2 | 33.4 | 32.1 | 34.2 |
| 212 ≤ X ≤ 350 | 19.9 | 39.8 | 38.7 | 36.7 |
| 75 ≤ X ≤ 212 | 24.9 | 14.3 | 13.7 | 14.5 |
| 0 ≤ X ≤ 75 | 50.7 | 0.5 | 0.4 | 0.7 |
| Total | 100.0 | 100.0 | 100.0 | 100.0 |

From the foregoing, a person skilled in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A method for preparing L-amino acid granules, wherein the L-amino acid is one or more selected from the group consisting of L-threonine, L-tryptophan, L-methionine, L-valine, L-tyrosine, L-phenylalanine, L-isoleucine, and L-leucine, the method comprising:

(a) preparing a fermentation liquid of L-amino acid;
(b) removing moisture from the fermentation liquid of L-amino acid such that the solid content of the fermentation liquid of L-amino acid is in a range of 20% to 90%, to obtain a concentrated fermentation liquid;
(c) forming granulated particles with a moisture content of 0% to 40% by mixing the concentrated fermentation liquid of L-amino acid with a seed;
(d) drying the granulated particles formed in Step (c);
(e) sieving the granulated particles dried in Step (d); and pulverizing or circulating the particles left in step (e) to be recycled as the seed in step (c).

2. The method according to claim 1, wherein the fermentation liquid of L-amino acids in Step (a) is obtained through the fermentation of a strain of the genus *Corynebacterium*.

3. The method according to claim 1, wherein in Step (b) is performed by a concentration method or slurry-drying method.

4. The method according to claim 1, wherein in the seed of Step (c), the particles with a particle size of 75 μm or less are present in a range of 9% or higher.

5. The method according to claim 1, wherein in the seed of Step (c), the particles with a particle size of 212 μm or less are present in a range of 97% or less.

6. The method according to claim 1, wherein the size of the particles obtained in Step (c) is adjusted by the particle size of the seed, the mixing ratio of the seed to the slurry, or the mixing ratio of the seed to the solid content of the slurry.

7. The method according to claim 6, wherein the mixing ratio of the seed to the slurry of Step (c) is in a range of 1 to 15.

8. The method according to claim 6, wherein the mixing ratio of the seed to the solid content of the slurry of Step (c) is in a range of 2.8 to 22.

9. The method according to claim 1, wherein the moisture content of the particles obtained in Step (c) is in a range of 1% to 30%.

10. The method according to claim 1, wherein with regard to the particle size of the granulated particles of Step (c), the particles with a particle size of 2,000 μm or higher are present in an amount of 1.0% or less and the particles with a particle size of 75 μm or less are present in a range of 5.0% or less.

11. The method according to claim 1, wherein with regard to the particle size of the granulated particles of Step (c), the particles with a particle size greater than 75 μm are present in a range of 50% or higher.

12. The method according to claim 1, wherein Step (d) is performed at a temperature of 60° C. to 90° C.

13. The method according to claim 1, wherein the fermentation liquid in Step (a) comprises the microorganism.

* * * * *